United States Patent
Nitta et al.

(10) Patent No.: US 11,692,687 B2
(45) Date of Patent: Jul. 4, 2023

(54) WAVELENGTH CONVERTING COMPOSITE MEMBER, AND LIGHT EMITTING DEVICE AND ELECTRONIC INSTRUMENT EMPLOYING SAME

(71) Applicant: Panasonic Intellectual Property Management Co., Ltd., Osaka (JP)

(72) Inventors: Mitsuru Nitta, Kyoto (JP); Shozo Oshio, Osaka (JP); Chigusa Fujiwara, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 17/919,999

(22) PCT Filed: Apr. 19, 2021

(86) PCT No.: PCT/JP2021/015835
§ 371 (c)(1),
(2) Date: Oct. 19, 2022

(87) PCT Pub. No.: WO2021/215386
PCT Pub. Date: Oct. 28, 2021

(65) Prior Publication Data
US 2023/0160558 A1    May 25, 2023

(30) Foreign Application Priority Data
Apr. 23, 2020  (JP) ................. 2020-076772

(51) Int. Cl.
*F21V 9/38*    (2018.01)
*A61B 90/30*   (2016.01)

(52) U.S. Cl.
CPC .......... *F21V 9/38* (2018.02); *A61B 2090/304* (2016.02)

(58) Field of Classification Search
CPC ........................................... F21V 9/38
(Continued)

(56) References Cited

U.S. PATENT DOCUMENTS

| 11,269,246 B2* | 3/2022 | Hsu ................. G03B 33/08 |
| 2005/0122485 A1* | 6/2005 | Kao ................. G03B 21/14 |
| | | 353/84 |

(Continued)

FOREIGN PATENT DOCUMENTS

| JP | 1-105935 A | 4/1989 |
| JP | 2016-161709 A | 9/2016 |
| JP | 2019-101201 A | 6/2019 |

OTHER PUBLICATIONS

International Search Report for corresponding Application No. PCT/JP2021/015835, dated Jun. 15, 2021.
(Continued)

*Primary Examiner* — Christopher M Raabe
(74) *Attorney, Agent, or Firm* — Renner, Otto, Boisselle & Sklar, LLP

(57) ABSTRACT

Provided is a wavelength converting composite member including: a disk-shaped substrate; a first wavelength converting member provided on the substrate and containing a first phosphor that radiates fluorescence due to a parity-forbidden transition; and a second wavelength converting member provided on the substrate and containing a second phosphor that radiates fluorescence due to a parity-allowed transition. The first wavelength converting member and the second wavelength converting member are disposed adjacent to each other along the circumferential direction of the substrate. The first wavelength converting member and the second wavelength converting member are provided on the substrate in such a way that the position of the center of gravity of the entirety of the first wavelength converting member and the second wavelength converting member is (Continued)

located on the rotation axis of the substrate. A light emitting device is provided with the wavelength converting composite member.

12 Claims, 9 Drawing Sheets

(58) Field of Classification Search
USPC .......................................................... 362/84
See application file for complete search history.

(56) References Cited

U.S. PATENT DOCUMENTS

| | | | |
|---|---|---|---|
| 2009/0021851 A1* | 1/2009 | Janicek | G02B 26/008 |
| | | | 359/892 |
| 2017/0059979 A1* | 3/2017 | Hsu | G02B 26/008 |
| 2019/0171097 A1 | 6/2019 | Fujii | |
| 2019/0268576 A1* | 8/2019 | Ikeura | H04N 9/3105 |

OTHER PUBLICATIONS

Written Opinion for corresponding Application No. PCT/JP2021/015835, dated Jun. 15, 2021.

\* cited by examiner (a)

(b)

(a)

(b)

(a)

(b)

(a)

(b)

(a)

(b)

(a)

(b)

WAVELENGTH CONVERTING COMPOSITE MEMBER, AND LIGHT EMITTING DEVICE AND ELECTRONIC INSTRUMENT EMPLOYING SAME

TECHNICAL FIELD

The present invention relates to a wavelength converting composite member, and a light emitting device and an electronic instrument using the wavelength converting composite member.

BACKGROUND ART

There are conventionally known light emitting devices which combine a solid-state light emitting element that radiates primary light such as laser light, and a wavelength converting member that includes a phosphor. Known examples of such light emitting devices include laser lighting devices and laser projectors. Also, a phosphor wheel type of wavelength converting member that is rotated by a motor is used in such light emitting devices.

Patent Literature 1 discloses a light source device provided with a light source and a phosphor wheel having a first substrate and a second substrate. The phosphor wheel has a first phosphor and a second phosphor disposed between the first substrate and the second substrate, and the first phosphor and the second phosphor are disposed at different positions in the rotation direction of the phosphor wheel. Also, the first phosphor is in contact with the first substrate and the second substrate, and the second phosphor is in contact with the second substrate. According to a configuration such as this, heat generated by the phosphors is less likely to have an effect and a decrease in light emission efficiency is suppressed.

CITATION LIST

Patent Literature

Patent Literature 1: Japanese Unexamined Patent Application Publication No. 2016-161709

SUMMARY OF INVENTION

Technical Problem

In Patent Literature 1, a configuration is adopted in which, when the first phosphor and the second phosphor are viewed along the rotation axis of the phosphor wheel, the area of the first phosphor is smaller than the area of the second phosphor, and in addition the thickness of the first phosphor is greater than the thickness of the second phosphor. Furthermore, when viewed along the rotation axis, in the first substrate and the second substrate, there are regions where neither the first phosphor nor the second phosphor is in contact, that is, regions where there is no phosphor. Therefore, the center of gravity of a phosphor layer composed of the first phosphor and the second phosphor may be located at a position deviated from the rotation axis of the phosphor wheel. Thus, when the phosphor wheel of Patent Literature 1 is rotated by a rotation drive device, the rotation of the phosphor wheel becomes unstable due to the deviation between the rotation axis and the center of gravity, and therefore there is a problem in that high-speed rotation is not possible. Furthermore, there is a problem in that when the rotation of the phosphor wheel becomes unstable, the rotation drive device malfunctions.

The present invention has been made in consideration of such problems as described above, which are inherent in the prior art. Thus, an object of the present invention is to provide a wavelength converting composite member with which it is possible for a substrate provided with a wavelength converting member to be rotated smoothly to improve reliability, and to provide a light emitting device and an electronic instrument using the wavelength converting composite member.

To solve the above problems, a wavelength converting composite member according to a first aspect of the present invention includes: a disk-shaped substrate; a first wavelength converting member provided on the substrate and containing a first phosphor that radiates fluorescence due to a parity-forbidden transition; and a second wavelength converting member provided on the substrate and containing a second phosphor that radiates fluorescence due to a parity-allowed transition. The first wavelength converting member and the second wavelength converting member are disposed adjacent to each other along the circumferential direction of the substrate. The first wavelength converting member and the second wavelength converting member are provided on the substrate in such a way that the position of the center of gravity of the entirety of the first wavelength converting member and the second wavelength converting member is located on the rotation axis of the substrate.

A light emitting device according to a second aspect of the present invention includes the wavelength converting composite member.

An electronic instrument according to a third aspect of the present invention includes the light emitting device.

BRIEF DESCRIPTION OF DRAWINGS

FIG. 4(a) is a plan view and FIG. 4(b) is a cross-sectional view.

FIG. 5(a) is a plan view and FIG. 5(b) is a cross-sectional view.

DESCRIPTION OF EMBODIMENTS

Figure 1:
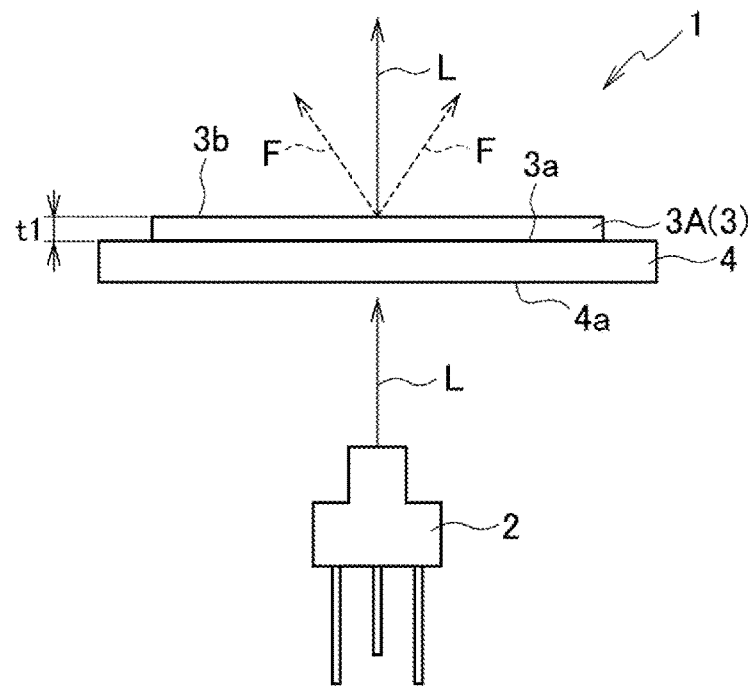
FIG. 1(a) is a schematic diagram illustrating a light emitting device provided with a wavelength converting member including a phosphor that radiates fluorescence due to a parity-allowed transition.
FIG. 1(b) is a schematic diagram illustrating a light emitting device provided with a wavelength converting member including a phosphor that radiates fluorescence due to a parity-forbidden transition.
Figure 1:
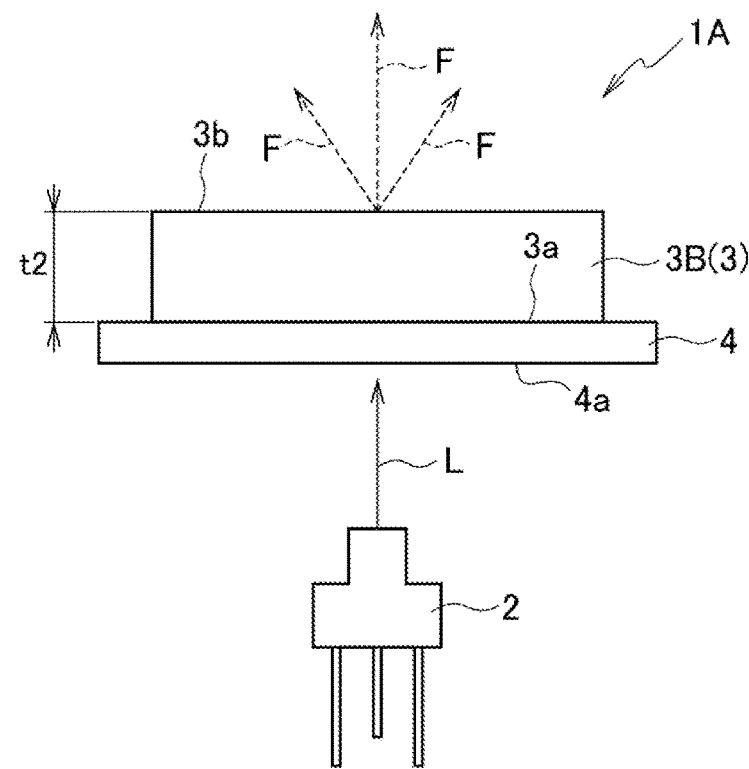

Using the drawings, a detailed description is given below of a wavelength converting composite member according to this embodiment, and a light emitting device and an electronic instrument using the wavelength converting composite member. Note that dimensional ratios in the drawings are exaggerated for convenience of explanation and are sometimes different from actual ratios.

A possible example of a light emitting device obtained by combining a light emitting element and a phosphor is one provided with a solid-state light emitting element 2 that radiates primary light, a wavelength converting member 3 that includes a phosphor, and a substrate 4 that holds the wavelength converting member 3 on a surface thereof, as illustrated in FIG. 1.

The solid-state light emitting element 2 is a light emitting element that radiates laser light L as primary light, and for example, a laser diode such as a surface emitting laser diode can be used. The wavelength converting member 3 receives the laser light L, and thereby radiates fluorescence F having a longer wavelength than that of the laser light L. That is, the wavelength converting member 3 receives the laser light L at a front surface 3a, and radiates the fluorescence F from a back surface 3b. The substrate 4 has a degree of transparency with which it is possible for the laser light L to pass therethrough, and is configured such that the laser light L that is input from a main surface 4a, which is a surface of the substrate 4, passes therethrough. As the transparent substrate 4, for example, a quartz substrate, a sapphire substrate, or a translucent fluorescent ceramic substrate can be used.

In this kind of light emitting device 1, the laser light L radiated on the substrate 4 passes through the substrate 4 and the wavelength converting member 3. Then, when the laser light L passes through the wavelength converting member 3, phosphor included in the wavelength converting member 3 absorbs part of the laser light L and radiates the fluorescence F. The light emitting device 1 thereby radiates light including the laser light L and the fluorescence F, as output light. Therefore, for example, when the laser light L is blue and the fluorescence F is yellow, white output light is radiated due to additive color mixing of the laser light L and the fluorescence F.

Here, when the phosphor included in the wavelength converting member 3 (3A) is a phosphor that radiates fluorescence due to a parity-allowed transition, the phosphor can efficiently absorb the laser light L because the transition probability is high. That is, if the phosphor is, for example, yttrium aluminum garnet activated with $Ce^{3+}$ ($Y_3Al_2(AlO_4)_3:Ce^{3+}$, YAG:$Ce^{3+}$), the phosphor absorbs approximately 90% of blue laser light L and radiates yellow fluorescence F. Therefore, as illustrated in FIG. 1(*a*), in the light emitting device 1, when the phosphor included in the wavelength converting member 3A is a phosphor that radiates fluorescence due to a parity-allowed transition, the thickness of the wavelength converting member 3A can be comparatively thin. Specifically, the wavelength converting member 3A can have a thickness t1 of 50 μM to 100 μm, for example.

In contrast, when the phosphor included in the wavelength converting member 3 (3B) is a phosphor that radiates fluorescence due to a parity-forbidden transition, the phosphor cannot efficiently absorb the laser light L because the transition probability is low. That is, if the phosphor is a $(Gd,La)_3(Ga,Sc)_2(GaO_4)_3:Cr^{3+}$ phosphor (GSG phosphor) activated with $Cr^{3+}$, the phosphor absorbs approximately 60% of blue laser light L and radiates near-infrared fluorescence F. Therefore, as illustrated in FIG. 1(*b*), in a light emitting device 1A, when the phosphor included in the wavelength converting member 3B is a phosphor that radiates fluorescence due to a parity-forbidden transition, it is necessary for the thickness of the wavelength converting member 3B to be comparatively thick to increase the wavelength conversion efficiency. Specifically, it is necessary for the wavelength converting member 3B to have a thickness t2 of 300 μm to 400 μm, for example.

Figure 2:
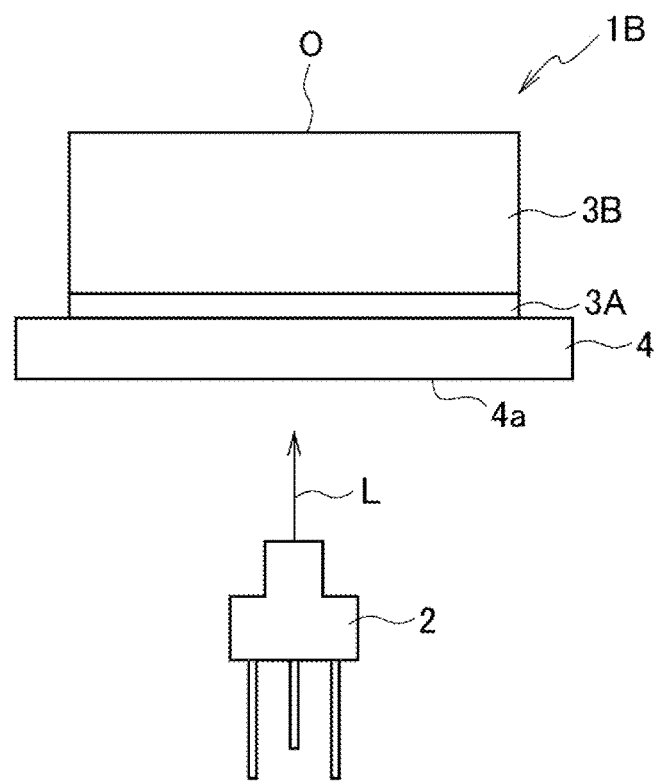
FIG. 2 is a schematic diagram of a light emitting device provided with both a wavelength converting member including a phosphor that radiates fluorescence due to a parity-allowed transition, and a wavelength converting member including a phosphor that radiates fluorescence due to a parity-forbidden transition.
Figure 2:
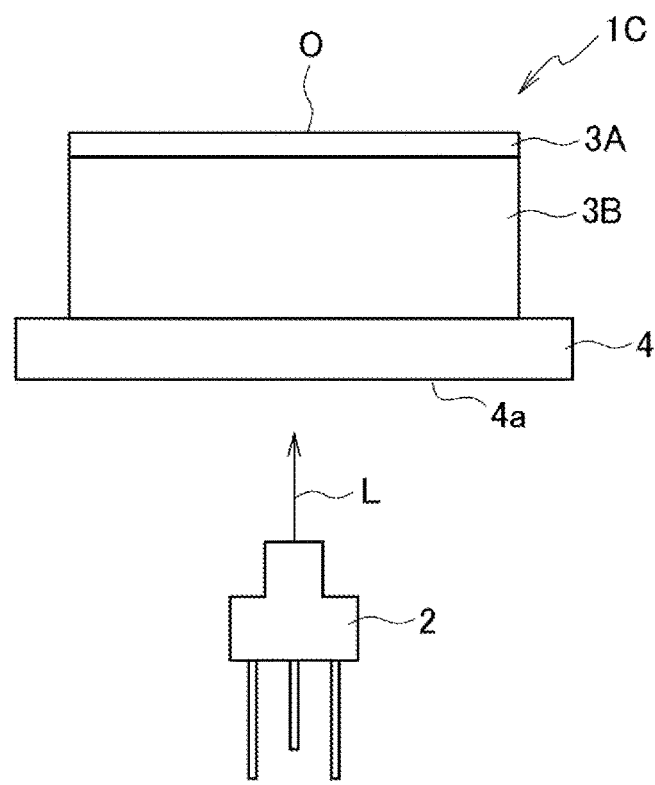

Here, by combining the solid-state light emitting element 2, the wavelength converting member 3A, and the wavelength converting member 3B described above, it is possible to obtain a light emitting device capable of radiating both white light and near-infrared light as output light. Specifically, a light emitting element that radiates blue laser light L is used as the solid-state light emitting element 2, a member including YAG:$Ce^{3+}$ phosphor is used as the wavelength converting member 3A, and a member including GSG phosphor is used as the wavelength converting member 3B. Then, as illustrated in FIG. 2, the wavelength converting member 3A and the wavelength converting member 3B are stacked on the transparent substrate 4. In a light emitting device 1B illustrated in FIG. 2(*a*), the wavelength converting member 3A is stacked above the substrate 4, and the wavelength converting member 3B is further stacked above the wavelength converting member 3A. In a light emitting device 1C illustrated in FIG. 2(*b*), the wavelength converting member 3B is stacked above the substrate 4, and the wavelength converting member 3A is further stacked above the wavelength converting member 3B.

With respect to such light emitting devices 1B and 1C, when blue laser light L is radiated from the main surface (lower surface) 4a of the substrate 4, the radiated laser light L passes through the substrate 4 and the wavelength converting members 3A and 3B. When the laser light L passes through the wavelength converting member 3A, the YAG:$Ce^{3+}$ phosphor included in the wavelength converting member 3A absorbs part of the laser light L and radiates yellow fluorescence. Furthermore, when the laser light L passes through the wavelength converting member 3B, the GSG phosphor in the wavelength converting member 3B absorbs part of the laser light L and radiates near-infrared fluorescence. Therefore, the light emitting devices of FIG. 2 can emit both white light generated by additive color mixing of the laser light L and yellow fluorescence, and near-infrared light from a light output surface O.

As mentioned above, the phosphor included in the wavelength converting member 3A is a phosphor that radiates fluorescence due to a parity-allowed transition, and therefore the thickness of the wavelength converting member 3A can be comparatively thin. In contrast, the phosphor included in the wavelength converting member 3B is a phosphor that radiates fluorescence due to a parity-forbidden transition, and it is therefore necessary for the thickness of the wavelength converting member 3B to be comparatively thick to increase the wavelength conversion efficiency. Therefore, in the light emitting device 1B illustrated in FIG. 2(a), yellow fluorescence radiated from the wavelength converting member 3A may be hindered by the thick-film wavelength converting member 3B and may not be able to sufficiently pass through the wavelength converting member 3B. Furthermore, in the light emitting device 1C illustrated in FIG. 2(b), the laser light L that has passed through the substrate 4 may be absorbed by the wavelength converting member 3B and may not be able to sufficiently reach the wavelength converting member 3A.

As described above, in the light emitting devices 1B and 1C illustrated in FIG. 2, the wavelength converting member 3A and the wavelength converting member 3B are stacked in the thickness direction of the substrate 4, and therefore there is a problem in that the extraction efficiency of white light decreases due to the thick-film wavelength converting member 3B.

The wavelength converting composite member of this embodiment is provided with a structure that is capable of increasing light extraction efficiency even when provided with both a wavelength converting member including a phosphor that radiates fluorescence due to a parity-allowed transition and a wavelength converting member including a phosphor that radiates fluorescence due to a parity-forbidden transition.

[Wavelength Converting Composite Member]

Figure 3:
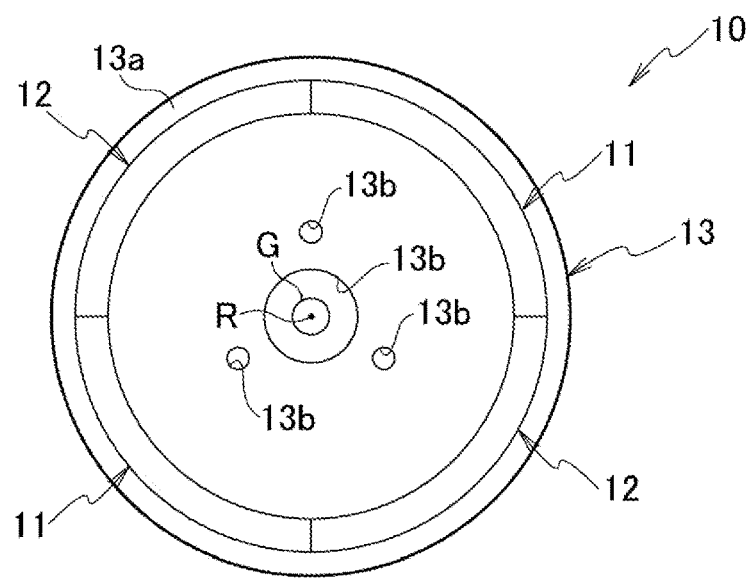
FIG. 3 is a plan view schematically illustrating an example of a wavelength converting composite member according to this embodiment.

As illustrated in FIG. 3, the wavelength converting composite member of this embodiment is provided with a disk-shaped substrate 13, and a first wavelength converting member 11 and a second wavelength converting member 12 provided on the substrate 13. The first wavelength converting member 11 and the second wavelength converting member 12 are fixed to one main surface 13a of the substrate 13.

The first wavelength converting member 11 and the second wavelength converting member 12 have a circular arc shape when viewed in plan view, and in addition are disposed adjacent to each other along the circumferential direction of the substrate 13. That is, in a wavelength converting composite member 10 illustrated in FIG. 3, the first wavelength converting member 11 and the second wavelength converting member 12 each form a circular arc shape divided into two parts. Also, the first wavelength converting member 11 and the second wavelength converting member 12 are disposed in an alternating manner along the peripheral edge of the substrate 13, and form a wavelength converting member having an annular shape as a whole.

Note that, in FIG. 3, although the first wavelength converting member 11 and the second wavelength converting member 12 form an annular shape in contact with each other, there may be a gap between the first wavelength converting member 11 and the second wavelength converting member 12.

The first wavelength converting member 11 contains a first phosphor that radiates fluorescence due to a parity-forbidden transition. As the first phosphor, it is possible to use a phosphor that radiates fluorescence based on the electron energy transition of a transition metal ion, and, for example, it is possible to use a phosphor including at least one ion selected from the group consisting of Cr, Mn, Fe, Cu, and Ni as an activator. Specifically, as the first phosphor, it is possible to use a phosphor including at least one of $Cr^{3+}$ or $Mn^{4+}$ as an activator. The emission of light by the first phosphor is caused by a parity-forbidden transition, and therefore the absorption rate of excitation light decreases. Note that although the matrix of the first phosphor is not particularly limited, it is possible to use at least one selected from the group consisting of oxides, sulfides, nitrides, halides, oxysulfides, oxynitrides, and acid halides, for example.

In detail, an activator of the first phosphor is a fluorescent ion that has the property of absorbing excitation light (primary light) emitted from the solid-state light emitting element and converting this into a light component having a longer wavelength than that of the excitation light. Also, the activator of the first phosphor is an ion capable of radiating fluorescence due to a parity-forbidden transition, and is preferably at least one of $Cr^{3+}$ or $Mn^{4+}$, for example.

Examples of the first phosphor include halophosphates, phosphates, halosilicates, silicates, aluminates, aluminosilicates, borates, germanates, silicate nitrides, aluminosilicate nitrides, silicate oxynitrides, and aluminosilicate oxynitrides having the above-mentioned activator added thereto. Therefore, it is sufficient for one suitable for the lighting design to be selected as appropriate from thereamong and used as the first phosphor.

Here, the activator of the first phosphor is preferably $Cr^{3+}$. Due to the use of $Cr^{3+}$, it is possible to obtain a first phosphor having the property of absorbing visible light, particularly blue light or red light, and converting this into a light component that is dark red to near infrared. Furthermore, it also becomes easy to change the light absorption peak wavelength and fluorescence peak wavelength of the phosphor depending on the type of matrix to which the activator is added, which is advantageous in changing the excitation spectrum shape and fluorescence spectrum shape. In addition, there are many known phosphors activated with $Cr^{3+}$ that absorb blue light or red light and convert this into a near-infrared fluorescent component. Therefore, not only does the selection of solid-state light emitting elements that emit primary light broaden, but it also becomes easy to change the peak wavelength of fluorescence emitted by the first phosphor, therefore resulting in a light emitting device that is advantageous in controlling the spectral distribution of output light.

Note that a phosphor having a fluorescent ion of $Cr^{3+}$ is not particularly limited as long as it absorbs excitation light and converts this into fluorescence having a longer wavelength than that of the excitation light, and may be selected as appropriate from known $Cr^{3+}$ activated phosphors. However, the $Cr^{3+}$ activated phosphor is preferably a phosphor for which the matrix is a composite metal oxide that is easy to manufacture.

The $Cr^{3+}$ activated phosphor is preferably a composite oxide phosphor having a garnet-type crystal structure which has been used in many practical applications. As this kind of $Cr^{3+}$ activated garnet phosphor, it is possible to use at least one selected from the group consisting of $Y_3Al_2(AlO_4)_3:Cr^{3+}$, $La_3Al_2(AlO_4)_3:Cr^{3+}$, $Gd_3Al_2(AlO_4)_3:Cr^{3+}$, $Y_3Ga_2(AlO_4)_3:Cr^{3+}$, $La_3Ga_2(AlO_4)_3:Cr^{3+}$, $Gd_3Ga_2(AlO_4)_3:Cr^{3+}$, $Y_3Sc_2(AlO_4)_3:Cr^{3+}$, $La_3Sc_2(AlO_4)_3:Cr^{3+}$, $Gd_3Sc_2(AlO_4)_3:Cr^{3+}$, $Y_3Ga_2(GaO_4)_3:Cr^{3+}$, $La_3Ga_2(GaO_4)_3:Cr^{3+}$, $(Gd,La)_3Ga_2(GaO_4)_3:Cr^{3+}$, $Gd_3Ga_2(GaO_4)_3:Cr^{3+}$, $Y_3Sc_2(GaO_4)_3:$ $Cr^{3+}$, $La_3Sc_2(GaO_4)_3:Cr^{3+}$, $Gd_3Sc_2(GaO_4)_3:Cr^{3+}$, and $(Gd, La)_3(Ga,Sc)_2(GaO_4)_3:O^{3+}$. Furthermore, the $Cr^{3+}$ activated garnet phosphor may also be a solid solution obtained with these phosphors as an end member.

The first wavelength converting member 11 can be prepared by sealing the first phosphor with a sealing material. The sealing material is preferably at least one of an organic material or an inorganic material, particularly a transparent (translucent) organic material or a transparent (translucent) inorganic material. An example of an organic sealing material is a transparent organic material such as silicone resin. An example of an inorganic sealing material is a transparent inorganic material such as low-melting-point glass.

Furthermore, as the first wavelength converting member 11, it is possible to use a sintered body having a plurality of voids therein, obtained by sintering the first phosphor. In addition, as the first wavelength converting member 11, it is also possible to use a ceramic body not having a plurality of voids therein, obtained by sintering the first phosphor. Due to the first wavelength converting member 11 being this kind of sintered body or ceramic body, the manufacturing and handling of the first wavelength converting member 11 becomes easy, therefore resulting in a wavelength converting member that is suitable for industrial production.

The second wavelength converting member 12 contains a second phosphor that radiates fluorescence due to a parity-allowed transition. As this kind of second phosphor, it is possible to use a phosphor including at least one selected from the group consisting of $Ce^{3+}$, $Eu^{2+}$, and $Yb^{2+}$ as an activator. The emission of light by the second phosphor is caused by a parity-allowed transition, and therefore the absorption rate of excitation light is high. Note that although the matrix of the second phosphor is not particularly limited, it is possible to use at least one selected from the group consisting of oxides, sulfides, nitrides, halides, oxysulfides, oxynitrides, and acid halides, for example.

In detail, an activator of the second phosphor is a fluorescent ion that has the property of absorbing excitation light (primary light) emitted from the solid-state light emitting element and converting this into a light component having a longer wavelength than that of the excitation light. Also, the activator of the second phosphor is an ion capable of radiating fluorescence due to a parity-allowed transition, and is preferably at least one selected from the group consisting of $Ce^{3\pm}$, $Eu^{2\pm}$, and $Yb^{2+}$, for example.

Examples of the second phosphor include halophosphates, phosphates, halosilicates, silicates, aluminates, aluminosilicates, borates, germanates, silicate nitrides, aluminosilicate nitrides, silicate oxynitrides, and aluminosilicate oxynitrides having the above-mentioned activator added thereto. Therefore, it is sufficient for one suitable for the lighting design to be selected as appropriate from thereamong and used as the second phosphor.

Note that a phosphor that is particularly preferred as the second phosphor is a composite oxide phosphor having a garnet-type crystal structure and having been activated with Ce'. As this kind of Ce' activated garnet phosphor, it is possible to use at least one compound selected from the group consisting of $Lu_3Al_2(AlO_4)_3:Ce^{3+}$, $Y_3Al_2(AlO_4)_3:Ce^{3+}$, $Lu_3Ga_2(AlO_4)_3:Ce^{3+}$, and $Y_3Ga_2(AlO_4)_3:Ce^{3+}$. Furthermore, the $Ce^{3+}$ activated garnet phosphor may also be a solid solution obtained with these phosphors as an end member.

Many $Ce^{3+}$ activated garnet phosphors have the property of absorbing blue light and converting this into light that is yellow to green. Furthermore, as mentioned above, many $Cr^{3+}$ activated garnet phosphors have the property of absorbing blue light or red light and converting this into light that is dark red to near infrared. Therefore, by using a solid-state light emitting element that emits blue light, a $Cr^{3+}$ activated garnet phosphor as the first phosphor, and a $Ce^{3+}$ activated garnet phosphor as the second phosphor, it is possible to obtain output light that includes light components constituting the three primary colors of light and a near-infrared light component.

Similar to the first wavelength converting member 11, the second wavelength converting member 12 can also be prepared by sealing the second phosphor with a sealing material. Furthermore, as the second wavelength converting member 12, it is possible to use a sintered body having a plurality of voids therein, obtained by sintering the second phosphor. In addition, as the second wavelength converting member 12, it is also possible to use a ceramic body not having a plurality of voids therein, obtained by sintering the second phosphor.

In the wavelength converting composite member 10, the disk-shaped substrate 13 has, in the central section, through-holes 13b that are directly or indirectly connected to an output shaft of a rotation drive device such as a motor. Then, for the substrate 13, it is possible to use a substrate having the characteristics of reflecting the excitation light emitted from the solid-state light emitting element and the fluorescence radiated from the first wavelength converting member 11 and the second wavelength converting member 12. That is, the substrate 13 can be a substrate that is light-reflective. This kind of substrate 13 is not particularly limited, but a substrate made of metal can be used, for example, and specifically a substrate made of aluminum can be used.

Furthermore, for the substrate 13, it is possible to use a substrate having the characteristics of transmitting the excitation light emitted from the solid-state light emitting element and the fluorescence radiated from the first wavelength converting member 11 and the second wavelength converting member 12. That is, the substrate 13 can be a substrate that is translucent. This kind of substrate 13 is not particularly limited, but a substrate made of quartz, sapphire, or a translucent fluorescent ceramic can be used, for example.

Here, in a case where the substrate 13 is light-reflective, a configuration is adopted in which, when excitation light is radiated on the first and second wavelength converting members 11 and 12, output light is emitted in the opposite direction to the irradiation direction of the excitation light. That is, in a wavelength converting composite member 10A illustrated in FIG. 4(b), a configuration is adopted in which, when excitation light is radiated from above downward to the first and second wavelength converting members 11 and 12, output light is emitted upward. Specifically, when excitation light is radiated from above toward a main surface 13c (upper surface) of the light-reflective substrate 13, the excitation light is radiated on the first and second wavelength converting members 11 and 12. Then, output light is radiated upward from the first and second wavelength converting members 11 and 12.

In contrast, in a case where the substrate 13 is translucent, when excitation light is radiated on the first and second wavelength converting members 11 and 12, output light is emitted in the same direction as the irradiation direction. That is, in the wavelength converting composite member 10A illustrated in FIG. 4(b), when excitation light is radiated from below upward to the first and second wavelength converting members 11 and 12, output light is emitted upward. Specifically, when excitation light is radiated from another main surface 13c (lower surface) of the translucent substrate 13, the excitation light passes through the substrate 13 and is radiated on the first and second wavelength converting members 11 and 12. Then, output light is radiated upward from the first and second wavelength converting members 11 and 12.

As mentioned above, in the wavelength converting composite member 10, the first wavelength converting member 11 and the second wavelength converting member 12 are disposed in an annular shape on the main surface 13a of the disk-shaped substrate 13. Therefore, by rotating the wavelength converting composite member 10 using a rotation drive device, output light including both fluorescence emitted from the first wavelength converting member 11 and the second wavelength converting member 12 can be radiated. Furthermore, by rotating the wavelength converting composite member 10, the effective surface area of the phosphors included in the first wavelength converting member 11 and the second wavelength converting member 12 can be expanded to promote heat exchange with air. As a result, temperature quenching of the first phosphor and the second phosphor can be suppressed and the emission of light by the phosphors can be carried out efficiently.

Here, in the wavelength converting composite member 10, the first wavelength converting member 11 and the second wavelength converting member 12 are provided on the main surface 13a of the substrate 13 in such a way that the position of the center of gravity of the entirety of the first wavelength converting member 11 and the second wavelength converting member 12 is located on a rotation axis R of the substrate 13.

As mentioned above, the first phosphor included in the first wavelength converting member 11 is a phosphor that radiates fluorescence due to a parity-forbidden transition. Therefore, the first phosphor cannot efficiently absorb the excitation light radiated from the solid-state light emitting element, and it is necessary for the first wavelength converting member 11 to contain a large amount of the first phosphor. In contrast, the second phosphor included in the second wavelength converting member 12 is a phosphor that radiates fluorescence due to a parity-allowed transition. Therefore, the second phosphor can efficiently absorb the excitation light radiated from the solid-state light emitting element, and it is therefore not necessary for the second wavelength converting member 12 to contain a large amount of the second phosphor. Thus, the overall mass of the first wavelength converting member 11 is greater than the overall mass of the second wavelength converting member 12.

Therefore, in the wavelength converting composite member 10, the first wavelength converting member 11 and the second wavelength converting member 12 are disposed in such a way that the position of the center of gravity G of the entirety of the first wavelength converting member 11 and the second wavelength converting member 12 is located on the rotation axis R of the substrate 13. Specifically, as illustrated in FIG. 3, in the wavelength converting composite member 10, the first wavelength converting member 11 and the second wavelength converting member 12 are each divided into two parts. Also, each part of the first wavelength converting member 11 and the second wavelength converting member 12 forms a circular arc shape with a center angle of approximately 90 degrees. Also, the first wavelength converting member 11 and the second wavelength converting member 12 are disposed in an alternating manner along the peripheral edge of the substrate 13, and form a wavelength converting member having an annular shape as a whole. That is, two first wavelength converting members 11 are disposed in a state of point symmetry about the rotation axis R. Similarly, two second wavelength converting members 12 are disposed in a state of point symmetry about the rotation axis R.

In this way, by dividing the first wavelength converting member 11 and the second wavelength converting member 12 each into two parts and disposing them in point symmetry, the position of the center of gravity G of the entirety of the first wavelength converting member 11 and the second wavelength converting member 12 is located on the rotation axis R of the substrate 13. Therefore, even when the wavelength converting composite member 10 is rotated using a rotation drive device, the rotation of the wavelength converting composite member 10 is unlikely to become unstable, and high-speed rotation therefore becomes possible.

Figure 4:
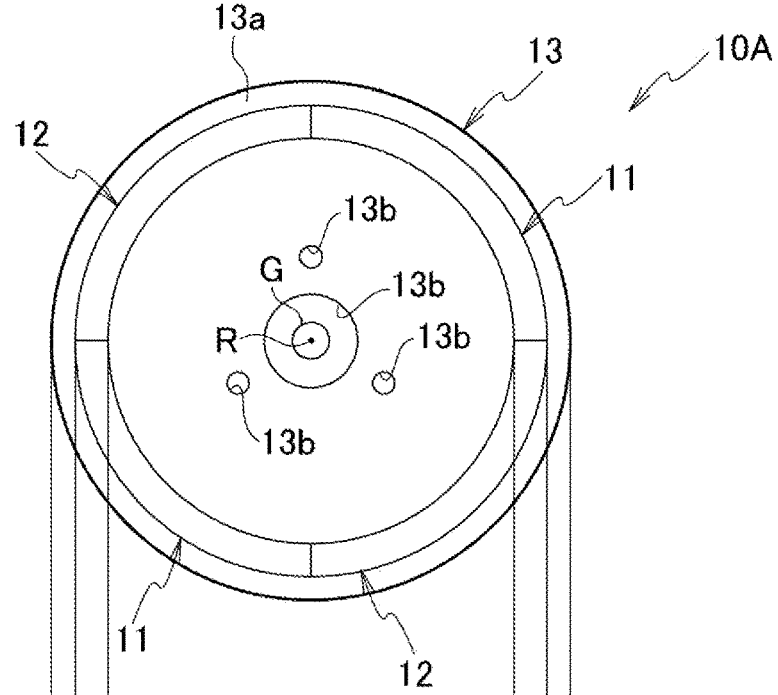
FIG. 4 is a diagram schematically illustrating another example of a wavelength converting composite member according to this embodiment.
Figure 4:
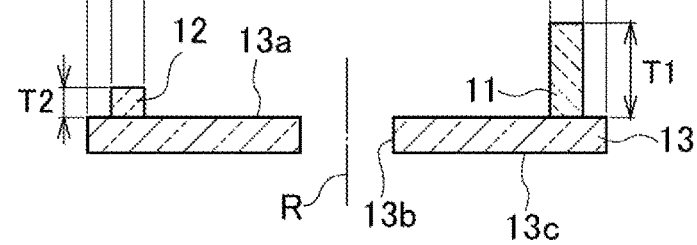

As mentioned above, the first phosphor has a low transition probability and also a low absorption rate of excitation light, and therefore the first wavelength converting member 11 preferably contains a large amount of the first phosphor to increase the absorption rate. In contrast, the second phosphor has a high transition probability and also a high absorption rate of excitation light, and it is therefore not necessary for the second wavelength converting member 12 to contain a large amount of the second phosphor as in the case of the first wavelength converting member 11. Therefore, as illustrated in FIG. 4, the first wavelength converting member 11 is preferably thicker than the second wavelength converting member 12 in the direction perpendicular to the main surface 13a of the substrate 13. Thus, due to the first wavelength converting member 11 having an increased thickness, it becomes possible to increase the absorption rate of excitation light and to efficiently emit fluorescence.

Furthermore, as mentioned above, in the wavelength converting composite member 10A, the first and second wavelength converting members 11 and 12 are disposed in such a way that the position of the center of gravity G of the entirety of the first and second wavelength converting members 11 and 12 is located on the rotation axis R of the substrate 13. Therefore, even when the thickness of the first wavelength converting member 11 is greater than that of the second wavelength converting member 12, it becomes possible for the wavelength converting composite member 10A to be stably rotated.

A thickness T1 of the first wavelength converting member 11 and a thickness T2 of the second wavelength converting member 12 can be set as appropriate from the type of the first phosphor and the second phosphor and the density of the phosphors in the wavelength converting members. The thickness T1 of the first wavelength converting member 11 can be 300 µm to 400 µm, for example. Furthermore, the thickness T2 of the second wavelength converting member 12 can be 50 µm to 100 µm, for example.

Figure 5:
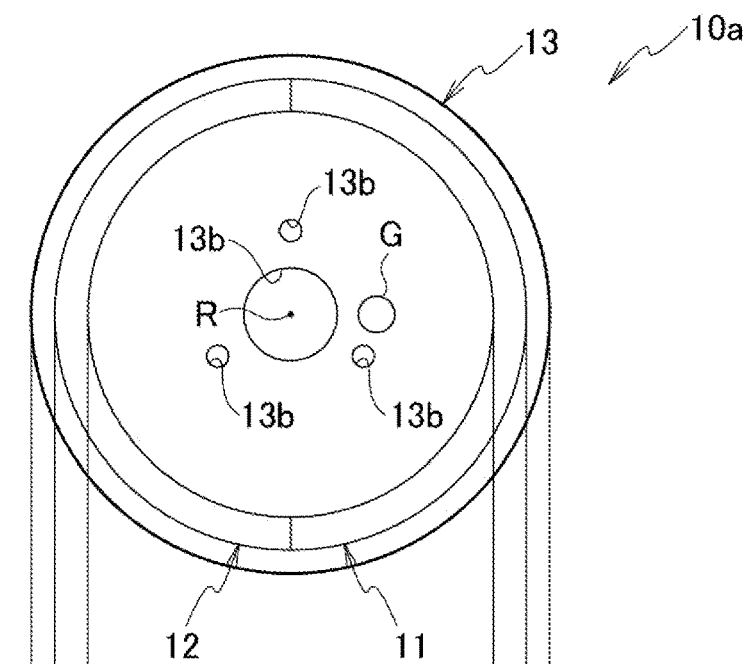
FIG. 5 is a diagram schematically illustrating a wavelength converting composite member according to a comparative example.
Figure 5:
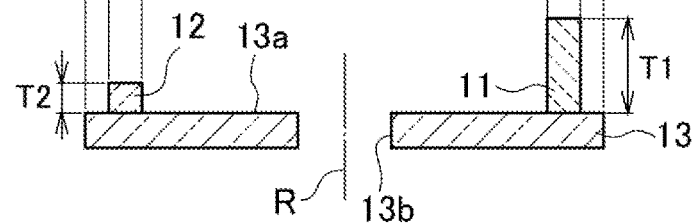

Here, FIG. 5 illustrates a wavelength converting composite member 10a according to a comparative example. In the wavelength converting composite member 10a, the first wavelength converting member 11 and the second wavelength converting member 12 each form a circular arc shape with a center angle of approximately 180 degrees. Furthermore, the thickness T1 of the first wavelength converting member 11 is greater than the thickness T2 of the second wavelength converting member 12. Therefore, the overall mass of the first wavelength converting member 11 is greater than the overall mass of the second wavelength converting member 12. Thus, the position of the center of gravity G of the entirety of the first wavelength converting member 11 and the second wavelength converting member 12 is biased more toward the first wavelength converting member 11 than the rotation axis R. Therefore, when the wavelength converting composite member 10a is rotated, the rotation becomes unstable due to the poor balance of the first wavelength converting member 11 and the second wavelength converting member 12. As a result, the rotation drive device linked to the wavelength converting composite member 10a may malfunction.

Figure 6:
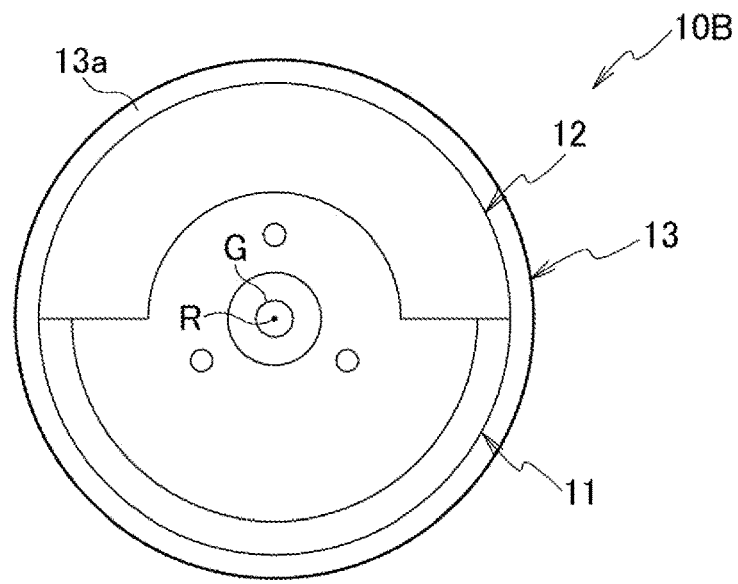
FIG. 6 is a plan view schematically illustrating another example of a wavelength converting composite member according to this embodiment.

In the wavelength converting composite member of this embodiment, the method of adjusting the position of the center of gravity G of the entirety of the first wavelength converting member 11 and the second wavelength converting member 12 so as to be located on the rotation axis R is not limited to the method illustrated in FIGS. 3 and 4. For example, as illustrated in FIG. 6, in a wavelength converting composite member 10B, the area occupied by the second wavelength converting member 12 is preferably larger than the area occupied by the first wavelength converting member 11 when viewed along the rotation axis R of the substrate 13.

As mentioned above, the overall mass of the first wavelength converting member 11 tends to be greater than the overall mass of the second wavelength converting member 12. Therefore, by making the occupied area of the second wavelength converting member 12 larger than the occupied area of the first wavelength converting member 11, it becomes possible for the position of the center of gravity G of the entirety of the first and second wavelength converting members 11 and 12 to be located on the rotation axis R.

Figure 7:
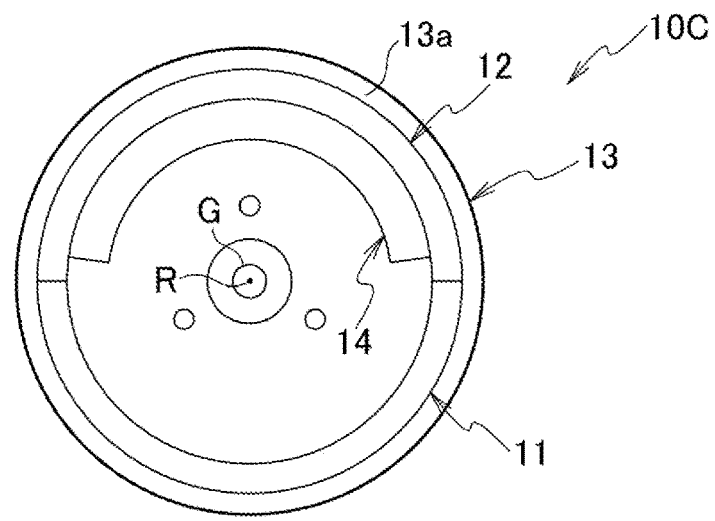
FIG. 7 is a plan view schematically illustrating another example of a wavelength converting composite member according to this embodiment.

A method such as that illustrated in FIG. 7 is another possible example of a method of adjusting the position of the center of gravity G of the entirety of the first and second wavelength converting members 11 and 12 so as to be located on the rotation axis R. In a wavelength converting composite member 10C of FIG. 7, due to a weight member 14 that does not include the first phosphor or the second phosphor being provided near the second wavelength converting member 12, the position of the center of gravity G of the entirety of the first wavelength converting member, the second wavelength converting member, and the weight member is located on the rotation axis R of the substrate.

The weight member 14 has a circular arc shape similar to the first and second wavelength converting members 11 and 12, and is provided along the second wavelength converting member 12, closer to the rotation axis R than the second wavelength converting member 12. Furthermore, the weight member 14 is provided in such a way as to be fixed to the main surface 13a of the substrate 13.

By using this kind of weight member 14, it becomes possible for the position of the center of gravity G of the entirety of the first and second wavelength converting members 11 and 12 to be located on the rotation axis R, and for the wavelength converting composite member 10C to be stably rotated. Note that it is sufficient for the weight member 14 to be a member made of a material that does not include a phosphor, and it is possible to use a member made of an organic material or an inorganic material, for example. Furthermore, the weight member 14 may be a member made of a translucent material, or a may be a member made of a light-reflective material.

Note that in the wavelength converting composite member 10C, the second wavelength converting member 12 and the weight member 14 are both fixed directly to the main surface 13a of the substrate 13 and are adjacent each other. However, the position of the weight member 14 is not limited to this mode, and the second wavelength converting member 12 and the weight member 14 may be stacked in the direction perpendicular to the main surface 13a of the substrate 13, for example. Furthermore, there may be a gap between the second wavelength converting member 12 and the weight member 14. In addition, the weight member 14 is not limited to a circular arc shape, and may have a rectangular shape or a circular shape.

Figure 8:
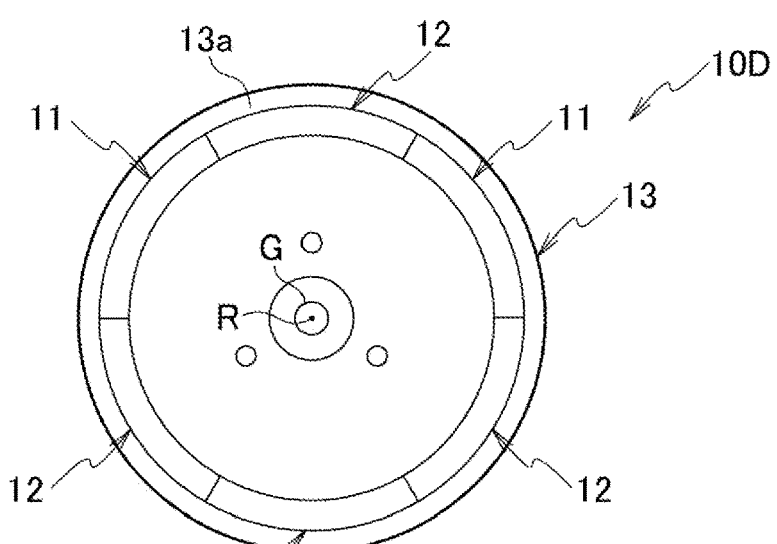
FIG. 8 is a plan view schematically illustrating another example of a wavelength converting composite member according to this embodiment.
Figure 8:
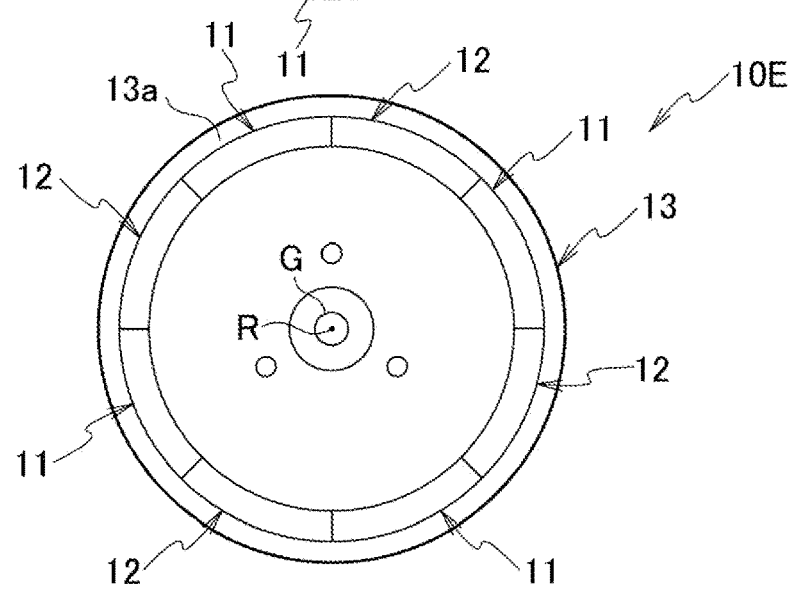

A method such as that illustrated in FIG. 8 is another possible example of a method of adjusting the position of the center of gravity G of the entirety of the first and second wavelength converting members 11 and 12 so as to be located on the rotation axis R. In wavelength converting composite members 10D and 10E of FIG. 8, the first wavelength converting member 11 and the second wavelength converting member 12 are each divided into a plurality of parts. Also, the first wavelength converting member 11 and the second wavelength converting member 12 are disposed in an alternating manner along the circumferential direction of the substrate 13.

Specifically, in the wavelength converting composite member 10D illustrated in FIG. 8(a), the first wavelength converting member 11 and the second wavelength converting member 12 are each divided into three parts. Also, each part of the first wavelength converting member 11 and the second wavelength converting member 12 forms a circular arc shape with a center angle of approximately 60 degrees. The first wavelength converting member 11 and the second wavelength converting member 12 are disposed in an alternating manner along the peripheral edge of the substrate 13, and form a wavelength converting member having an annular shape as a whole.

In the wavelength converting composite member 10E illustrated in FIG. 8(b), the first wavelength converting member 11 and the second wavelength converting member 42 are each divided into four parts. Also, each part of the first wavelength converting member 11 and the second wavelength converting member 12 forms a circular arc shape with a center angle of approximately 45 degrees. The first wavelength converting member 11 and the second wavelength converting member 12 are disposed in an alternating manner along the peripheral edge of the substrate 13, and form a wavelength converting member having an annular shape as a whole.

In this way, in the wavelength converting composite members 10D and 10E, the first wavelength converting member 11 and the second wavelength converting member 12 are each divided into a plurality of parts and disposed radially about the rotation axis R. Furthermore, the first wavelength converting member 11 and the second wavelength converting member 12 are disposed in an alternating manner along the circumferential direction of the substrate 13. It is thereby possible for the position of the center of gravity G of the entirety of the first wavelength converting member 11 and the second wavelength converting member 12 to be located on the rotation axis R of the substrate 13.

Note that the first wavelength converting member 11 and the second wavelength converting member 12 may each be divided into three parts as illustrated in FIG. 8(a), or may each be divided into four parts as illustrated in FIG. 8(b). Furthermore, the first wavelength converting member 11 and the second wavelength converting member 12 may each be divided into two parts as illustrated in FIG. 3, or may each be divided into five parts or six parts.

As mentioned above, in the wavelength converting composite member 10A illustrated in FIG. 4, a configuration is adopted in which the first wavelength converting member 11 has a greater thickness than the second wavelength converting member 12 in the direction perpendicular to the main surface 13a of the substrate 13. According to a configuration such as this, the first wavelength converting member 11 is able to efficiently radiate fluorescence due to an increased excitation light absorption efficiency.

Figure 9:
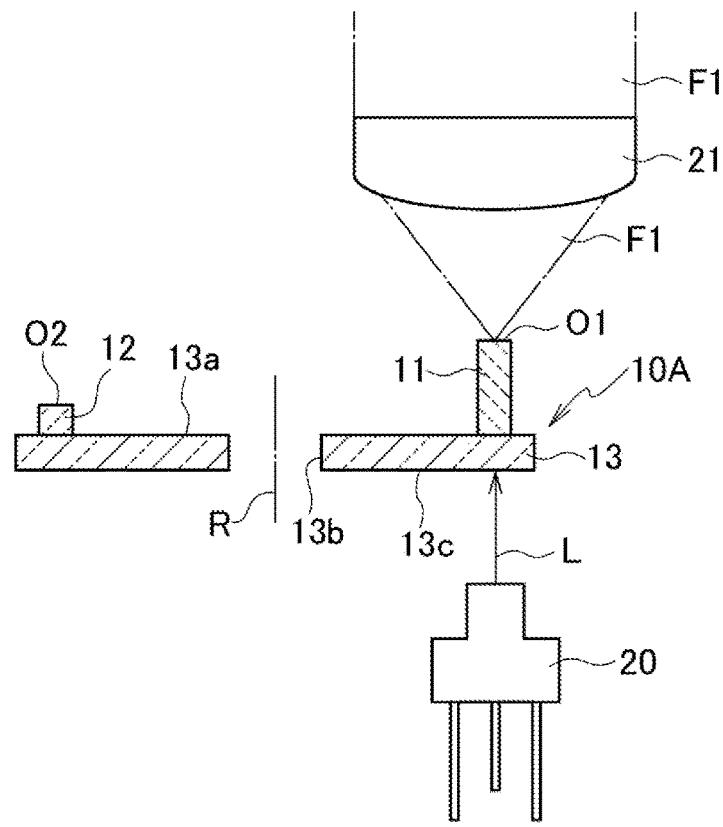
FIG. 9 is a cross-sectional view schematically illustrating a light emitting device using a wavelength converting composite member in which a first wavelength converting member and a second wavelength converting member have different heights.
Figure 9:
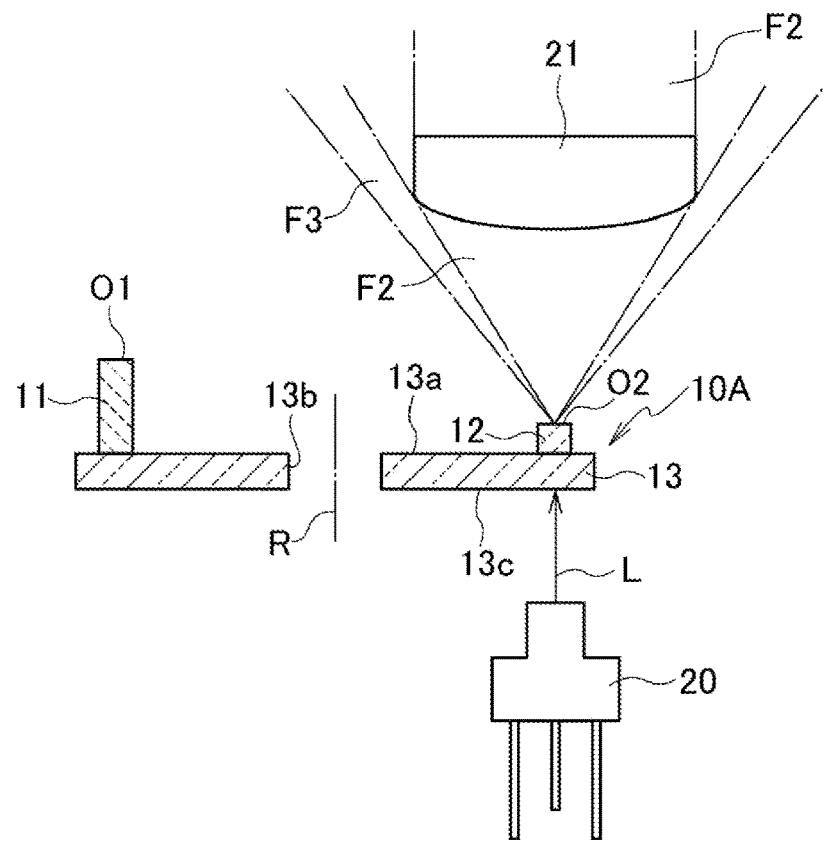

Here, FIG. 9 illustrates a light emitting device provided with the wavelength converting composite member 10A and a solid-state light emitting element 20 that radiates primary light L. This light emitting device has a configuration in which output light is emitted in a direction such that the primary light L emitted from the solid-state light emitting element 20 passes through the translucent substrate 13, the first wavelength converting member 11, and the second wavelength converting member 12.

Specifically, as illustrated in FIG. 9(a), primary light L radiated on the other main surface 13c (lower surface) of the substrate 13 passes through the substrate 13 and the first wavelength converting member 11. When the primary light L passes through the first wavelength converting member 11, the first phosphor included in the first wavelength converting member 11 absorbs at least part of the primary light L and radiates fluorescence. Then, output light F1 including fluorescence is radiated upward from a main light output surface O1 at an upper end of the first wavelength converting member 11. Thereafter, the output light F1 radiated from the main light output surface O1 passes through a lens 21 and is condensed.

Next, when the wavelength converting composite member 10A is rotated about the rotation axis R, as illustrated in FIG. 9(b), the primary light L radiated on the other main surface 13c of the substrate 13 passes through the substrate 13 and the second wavelength converting member 12. When the primary light L passes through the second wavelength converting member 12, the second phosphor included in the second wavelength converting member 12 absorbs at least part of the primary light L and radiates fluorescence. Then, output light F2 and F3 including fluorescence is radiated upward from a main light output surface O2 at an upper end of the second wavelength converting member 12. Thereafter, the output light radiated from the main light output surface O2 passes through the lens 21 and is condensed.

Here, in the light emitting device of FIG. 9, the distance between the substrate 13 of the wavelength converting composite member 10A and the lens 21 is constant. Also, in the wavelength converting composite member 10A, a configuration is adopted in which the thickness T1 of the first wavelength converting member 11 is greater than the thickness T2 of the second wavelength converting member 12. Therefore, the distance from the main light output surface O1 of the first wavelength converting member 11 to the lens 21 is shorter than the distance from the main light output surface O2 of the second wavelength converting member 12 to the lens 21. That is, the main light output surface O1 of the first wavelength converting member 11 is closer to the lens 21 than the main light output surface O2 of the second wavelength converting member 12.

Therefore, as illustrated in FIG. 9(a), the majority of the output light F1 radiated upward from the main light output surface O1 of the first wavelength converting member 11 is captured and condensed by the lens 21. In contrast, although the output light F2 radiated upward from the main light output surface O2 of the second wavelength converting member 12 is captured and condensed by the lens 21, the output light F3 is not captured by the lens 21. Therefore, the output light F3 is not condensed by the lens 21 and may not be used effectively.

Figure 10:
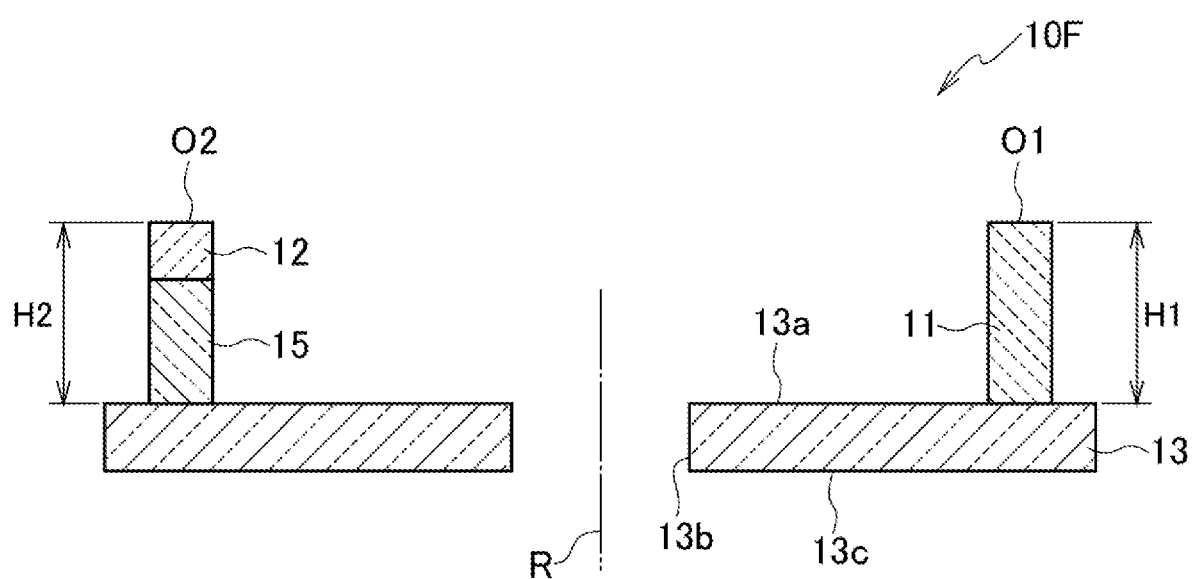
FIG. 10 is a cross-sectional view illustrating an example of a wavelength converting composite member according to this embodiment in which the heights of a first wavelength converting member and a second wavelength converting member are the same.

Thus, in the direction perpendicular to the main surface 13a of the substrate 13, the height from the main light output surface O1 of the first wavelength converting member 11 to the main surface 13a of the substrate 13 is preferably the same as the height from the main light output surface O2 of the second wavelength converting member 12 to the main surface 13a of the substrate 13. Specifically, as illustrated in FIG. 10, a height H1 from the main light output surface O1 of the first wavelength converting member 11 to the main surface 13a of the substrate 13 is preferably the same as a height H2 from the main light output surface O2 of the second wavelength converting member 12 to the main surface 13a of the substrate 13. As a result, the distance from the main light output surface O1 of the first wavelength converting member 11 to the lens 21 is the same as the distance from the main light output surface O2 of the second wavelength converting member 12 to the lens 21. Therefore, both the output light F1 radiated from the main light output surface O1 of the first wavelength converting member 11 and the output light F2 and F3 radiated from the main light output surface O2 of the second wavelength converting member 12 are captured and condensed by the lens 21. Therefore, it becomes possible for the output light F 1 and the output light F2 and F3 to be utilized effectively.

An example of a method of making the height H1 of the first wavelength converting member 11 and the height H2 of the second wavelength converting member 12 the same is a method in which a height adjustment member 15 for adjusting height is interposed between the main surface 13a of the substrate 13 and the second wavelength converting member 12, as illustrated in FIG. 10. As this kind of height adjustment member, a translucent member can be used, similar to the substrate 13. Note that when the substrate 13 is made of a light-reflective member, the height adjustment member 15 can also be a light-reflective member.

As described above, the wavelength converting composite members 10, 10A, 10B, 10C, 10D, 10E, and 10F of this embodiment are provided with the disk-shaped substrate 13, the first wavelength converting member 11, and the second wavelength converting member 12. The first wavelength converting member 11 contains a first phosphor that radiates fluorescence due to a parity-forbidden transition and is provided on the main surface 13a of the substrate 13. The second wavelength converting member 12 contains a second phosphor that radiates fluorescence due to a parity-allowed transition and is provided on the main surface 13a of the substrate 13. The first wavelength converting member 11 and the second wavelength converting member 12 are disposed adjacent to each other along the circumferential direction of the substrate 13. Also, the first wavelength converting member 11 and the second wavelength converting member 12 are provided on the main surface 13a of the substrate 13 in such a way that the position of the center of gravity G of the entirety of the first wavelength converting member 11 and the second wavelength converting member 12 is located on the rotation axis R of the substrate 13.

According to a configuration such as this, even when the wavelength converting composite members 10, 10A, 10B, 10C, 10D, 10E, and 10F are rotated using a rotation drive device, the rotation of the wavelength converting composite members is unlikely to become unstable, and therefore the wavelength converting composite members can be rotated smoothly to improve reliability. As a result, it becomes possible for the first phosphor in the first wavelength converting member 11 and the second phosphor in the second wavelength converting member 12 to be excited with high efficiency and for multiple types of fluorescence to be radiated from the same circumference.

Furthermore, the first phosphor in the first wavelength converting member 11 is a phosphor that radiates fluorescence due to a parity-forbidden transition. A possible example of this kind of phosphor is a phosphor having the property of absorbing blue light or red light and converting this into a light component that is dark red to near infrared. In addition, the second phosphor in the second wavelength converting member 12 is a phosphor that radiates fluorescence due to a parity-allowed transition. A possible example of this kind of phosphor is a phosphor having the property of absorbing blue light and converting this into a light component that is green, yellow, red, or the like. Therefore, by using the wavelength converting composite member of this embodiment, it is possible to obtain a light emitting device capable of radiating visible light such as white light and near-infrared light.

Note that the method of adjusting the position of the center of gravity G of the entirety of the first and second wavelength converting members 11 and 12 to be located on the rotation axis R in the wavelength converting composite member of this embodiment is not limited to the configurations illustrated in FIGS. 3 to 10. Furthermore, the configurations illustrated in FIGS. 3 to 10 may be combined in any manner such that the position of the center of gravity G of the entirety of the first and second wavelength converting members 11 and 12 is located on the rotation axis R.

[Light Emitting Device]

Next, the light emitting device according to this embodiment will be described. The light emitting device of this embodiment is provided with the wavelength converting composite member 10, 10A, 10B, 10C, 10D, 10E, or 10F described above. Furthermore, the light emitting device is preferably further provided with the solid-state light emitting element 20 that radiates light (primary light) with which the first wavelength converting member 11 and the second wavelength converting member 12 are irradiated. As this kind of solid-state light emitting element, it is possible to use an element that emits primary light having a maximum intensity within the range of 435 nm or more and less than 560 nm, preferably 440 nm or more and less than 480 nm.

For the solid-state light emitting element, it is possible to use a light emitting diode (LED), a laser diode, or the like. Also, by using an LED module or a laser diode that emits high-energy light of 1 W or more, for example, the resulting light emitting device can be expected to have a light output of a several hundred mW class. Furthermore, by using an LED module or the like that emits high-energy light of 3 W or more or 10 W or more, the resulting light emitting device can be expected to have a light output of a several W class. In addition, by using an LED module or the like that emits high-energy light of 30 W or more, the resulting light emitting device can be expected to have a light output exceeding 10 W. Furthermore, by using an LED module or the like that emits high-energy light of 100 W or more, the resulting light emitting device can be expected to have a light output exceeding 30 W.

When a laser diode is used as a solid-state light emitting element and the primary light is laser light, this results in a specification in which the first wavelength converting member 11 and the second wavelength converting member 12 are irradiated with high-density spot light. Therefore, the resulting light emitting device can be used as a high-output point light source, and it therefore becomes possible to expand the range of industrial uses of solid-state lighting. As this kind of laser diode, for example, it is possible to use an edge emitting laser (EEL), a vertical cavity surface emitting laser (VCSEL), or the like.

A light guide member such as an optical fiber may be interposed between the solid-state light emitting element and the wavelength converting composite member. It is thereby possible to adopt a structure in which the solid-state light emitting element and the wavelength converting composite member are spatially separated. Therefore, the light emitting part is light-weight and can be moved freely, and as a result it is possible to have a light emitting device with which it is easy for the irradiated location to be freely changed.

As mentioned above, in the light emitting device, the solid-state light emitting element is preferably at least one of a light emitting diode or a laser diode. However, the solid-state light emitting element is not limited thereto, and various kinds of light emitting elements can be used as long as they are capable of emitting high-output primary light.

Note that the number of solid-state light emitting elements provided in the light emitting device is not particularly limited, and there may be a single solid-state light emitting element or there may be multiple solid-state light emitting elements. By having a plurality of solid-state light emitting elements, it can be easy to increase the output of primary light, therefore resulting in a light emitting device that is advantageous for high output.

The number of solid-state light emitting elements is not particularly limited and may be selected as appropriate from, for example, 9 or more, 16 or more, 25 or more, 36 or more, 49 or more, 64 or more, 81 or more, or 100 or more. Furthermore, the upper limit for the number of solid-state light emitting elements is also not particularly limited and may be selected as appropriate from, for example, 9 or fewer, 16 or fewer, 25 or fewer, 36 or fewer, 49 or fewer, 64 or fewer, 81 or fewer, or 100 or fewer.

In the light emitting device, the solid-state light emitting element is preferably a surface emitting type of surface emitting light source. Variations in intensity distribution and unevenness in color tone of primary light radiated on the first wavelength converting member 11 and the second wavelength converting member 12 are thereby suppressed, and therefore the light emitting device is advantageous in suppressing uneven intensity distribution of output light.

Figure 11:
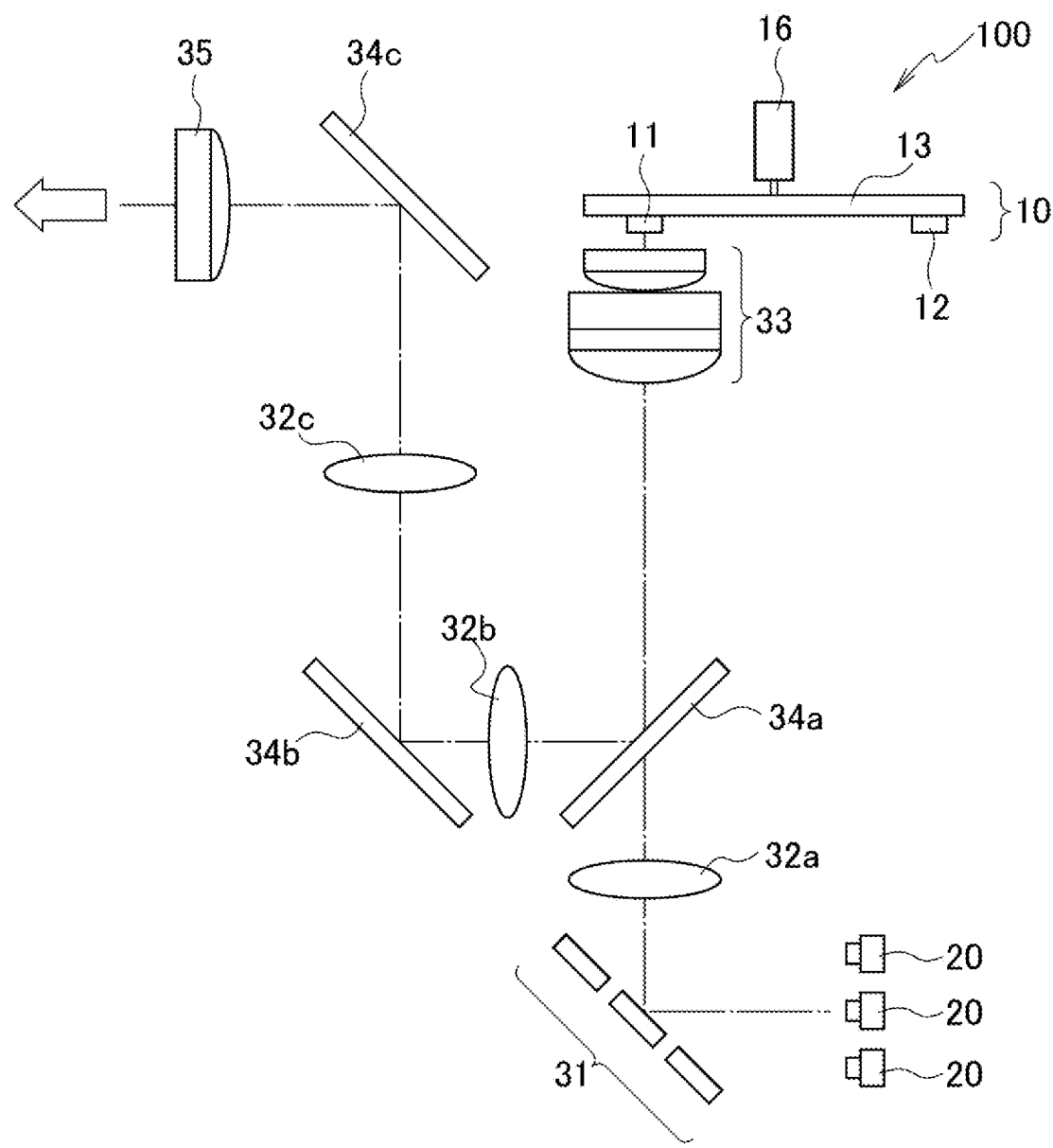
FIG. 11 is a schematic diagram illustrating an example of a light emitting device according to this embodiment.

FIG. 11 illustrates an example of a light emitting device according to this embodiment. In a light emitting device 100, primary light emitted by solid-state light emitting elements 20 is indirectly radiated on the first wavelength converting member 11 and the second wavelength converting member 12 in the wavelength converting composite member 10. A light component of which the wavelength is converted by the first wavelength converting member 11 and the second wavelength converting member 12 is then output.

In the light emitting device 100, a plurality of solid-state light emitting elements 20 are provided. Then, the primary light emitted by the solid-state light emitting elements 20 is reflected by a reflective mirror 31, condensed by a first lens 32a, and thereafter radiated on the first wavelength converting member 11 and the second wavelength converting member 12 formed on the main surface 13a of the substrate 13. The substrate 13 is light-reflective, and therefore the fluorescence emitted by the first wavelength converting member 11 and the second wavelength converting member 12 is reflected in the opposite direction to the direction in which the primary light emitted by the solid-state light emitting elements 20 is radiated.

The light component reflected by the substrate 13 is condensed by a condenser lens 33. Thereafter, the light component is repeatedly subjected to optical axis conversion and condensing by a first optical axis conversion mirror 34a, a second lens 32b, a second optical axis conversion mirror 34b, a third lens 32c, and a third optical axis conversion mirror 34c. The light component is then input to an output lens 35 and output from the light emitting device 100.

Here, in the light emitting device 100, the wavelength converting composite member 10 can be rotated using a rotation drive device 16. As mentioned above, in the wavelength converting composite member 10, the position of the center of gravity G of the entirety of the first and second wavelength converting members 11 and 12 is located on the rotation axis R of the substrate 13, and therefore the wavelength converting composite member 10 can be stably rotated. Therefore, in the light emitting device 100, it becomes possible for the first phosphor in the first wavelength converting member 11 and the phosphor in the second wavelength converting member 12 to be excited with high efficiency to radiate fluorescence.

Next, an improved example for an improvement in performance will be described in relation to the light emitting device of this embodiment.

The light emitting device of this embodiment can increase the absolute number of photons constituting the output light by means such as using a high output type of the solid-state light emitting elements 20 or increasing the number of solid-state light emitting elements 20. It is thereby possible for the light energy of the output light emitted from the light emitting device to exceed 3 W, preferably 10 W, and more preferably 30 W. By using this kind of high output type of light emitting device, irradiation can be performed with intense output light (for example, near-infrared light), and therefore a comparatively intense near-infrared ray can be radiated even when the distance to the object to be irradiated is large. Furthermore, the light emitting device also makes it easy to obtain information relating to the object to be irradiated, even if the object is very small or thick.

Furthermore, the light emitting device can also increase the photon density supplied to the phosphor by means such as using a light emitting element that emits primary light having a high light density such as a laser diode as the solid-state light emitting element 20, or by using an optical lens to condense the light emitted by the solid-state light emitting element 20. For example, it is possible for the light energy density of the primary light emitted by the solid-state light emitting element 20 to exceed 0.3 W/mm$^2$, preferably 1.0 W/mm$^2$, and more preferably 3.0 W/mm$^2$. In this case, because the light energy density of the primary light is high, the light emitting device radiates comparatively intense output light even with a configuration in which the first wavelength converting member 11 and the second wavelength converting member 12 are irradiated with optically diffused primary light. Furthermore, if a configuration is adopted in which the first wavelength converting member 11 and the second wavelength converting member 12 are irradiated with primary light that is not optically diffused, the light emitting device emits output light having a high light energy density. It is therefore possible to provide a light emitting device that can radiate output light over a large area, and a light emitting device that radiates output light having a high light energy density, while using a light emitting element having a small light output surface. In addition, the light emitting device is also capable of point output of near-infrared light having a high light energy density, for example. Note that although the upper limit of the light energy density of the primary light emitted by the solid-state light emitting element is not particularly limited, it can be 30 W/mm$^2$, for example.

Also, by using a solid-state light emitting element 20 that emits primary light having this kind of high light density, in the first wavelength converting member 11 and the second wavelength converting member 12, it is possible for the energy density of the emitted light to exceed 0.3 W/mm$^2$, preferably 1.0 W/mm$^2$, and more preferably 3.0 W/mm$^2$.

Note that by selecting an appropriate solid-state light emitting element, the intensity of light components in a region in which the wavelength is shorter than 440 nm in the output light can be adjusted to be less than 3% of the maximum fluorescence intensity. Furthermore, the intensity of light components in a region in which the wavelength is shorter than 440 nm in the output light can also be adjusted to be less than 1% of the maximum fluorescence intensity. Doing so results in output light having a near-zero intensity for light components in the ultraviolet to blue wavelength region, to which a photoresist is easily sensitive, and therefore the light emitting device emits near-infrared light which is advantageous for semiconductor-related inspection work and suitable for use in a yellow room and so forth.

The light emitting device of this embodiment may be further provided with a light distribution control mechanism that controls light distribution characteristics. If this kind of configuration is adopted, the light emitting device is advantageous in obtaining output light having desired light distribution characteristics, as a variable light distribution type of lighting system for in-vehicle use, for example.

The light emitting device of this embodiment may be further provided with a variable output intensity mechanism that changes the intensity of near-infrared rays, for example, such as an input power control device. If this kind of configuration is adopted, the light emitting device is advantageous for, for example, inspecting food products, drugs, and so forth, which are easily damaged by near-infrared irradiation.

The light emitting device of this embodiment may be further provided with a variable mechanism that changes the peak wavelength of a light component having a maximum fluorescence intensity in a wavelength range of 700 nm or more and less than 2500 nm. If this kind of configuration is adopted, the light emitting device becomes highly versatile and easily adaptable to miscellaneous uses. Furthermore, since the penetration depth of light into an object to be irradiated varies depending on the wavelength, the light emitting device is also advantageous for inspections in the depth direction of an object to be irradiated, and so forth. Note that, as this kind of a mechanism for varying the fluorescence peak wavelength, it is possible to use an optical filter such as a bandpass filter and a low-cut filter, for example.

The light emitting device of this embodiment may be further provided with a light control mechanism that performs ON-OFF control for the output of at least some wavelength components of the output light. If this kind of configuration is adopted, the light emitting device becomes highly versatile and easily adaptable to miscellaneous uses.

Note that in the light emitting device of this embodiment, visible light components having a wavelength of less than 700 nm and light components having a wavelength of 700 nm or more in the output light can be implemented as pulsed light. The half width of the pulsed light irradiation time can be less than 300 ms. Furthermore, it is also possible for the half width to become shorter as the magnitude of the output intensity of the output light becomes larger. Therefore, the half width can be less than 100 ms, less than 30 ms, less than 10 ms, less than 3 ms, or less than 1 ms, according to the output intensity of the output light. Note that the pulsed light non-irradiation time can be 1 ms or more and less than 10 s.

In this regard, it is reported that the human eye perceives light at 50 to 100 Hz (period of 20 to 10 ms) as flicker.

Furthermore, it is reported that birds such as pigeons perceive light at approximately 150 Hz (period of 6.7 ms) as flicker, and insects such as flies perceive light at approximately 300 Hz (period of 3.3 ms) as flicker. Therefore, one preferred form is a non-irradiation time of less than 30 ms which these creatures do not perceive as flicker.

On the other hand, intense light irradiation has the risk of damaging the illuminated object, and therefore for uses where it is not necessary to be concerned about flicker, a pulsed light non-irradiation time of 100 ms or longer, particularly 300 ms or longer, is a preferred form.

Note that the light energy of output light which is preferable for the purpose of beautification to adjust the growth of human hair and body hair is 0.01 J/cm$^2$ or more and less than 1 J/cm$^2$. Therefore, when the light energy of output light emitted from the light emitting device is in this range and the output light is irradiated near the hair root area, the light can be absorbed by melanin and so forth present inside the skin, and as a result the growth of hair and the like can be adjusted.

Here, a preferred 1/10 afterglow time of the output light, namely the time until the light intensity immediately before the light is turned off decreases in intensity to 1/10, is preferably less than 100 μs, more preferably less than 10 μs, and particularly preferably less than 1 μs. It is thereby possible to obtain a light emitting device that can be turned on and off instantaneously.

The light emitting device of this embodiment can also be further provided with an ultraviolet light source that radiates ultraviolet rays having a maximum intensity in the wavelength range of 120 nm or more and less than 380 nm, preferably 250 nm or more and less than 370 nm. In this way, the light emitting device can also have a sterilizing effect due to the ultraviolet rays.

The light emitting device of this embodiment is preferably a medical light emitting device. That is, the light emitting device of this embodiment, which is capable of emitting a near-infrared light component, can be a light source or lighting device for medical or biotechnological uses. In particular, the light emitting device of this embodiment can be a medical light emitting device used for a fluorescence imaging method or photodynamic therapy, or a biotechnological light emitting device used for inspection, assay, and so forth of cells, genes, specimens, and the like. A near-infrared light component has the property of passing through living organisms and cells, and therefore this kind of light emitting device can be used for observing and treating affected areas from outside the body and for biotechnology.

Furthermore, the light emitting device of this embodiment, which is capable of emitting a near-infrared light component, can also be used as a light source for a sensing system or as a lighting system for a sensing system. In this way, for example, the contents or foreign substances in a bag or container made of an organic substance can be inspected in an unopened state using a near-infrared light component that has the property of passing through organic substances or a near-infrared light component that is reflected by objects. Furthermore, with this kind of light emitting device, it is possible to, for example, monitor flora and fauna including people, and objects.

[Electronic Instrument]

Figure 12:
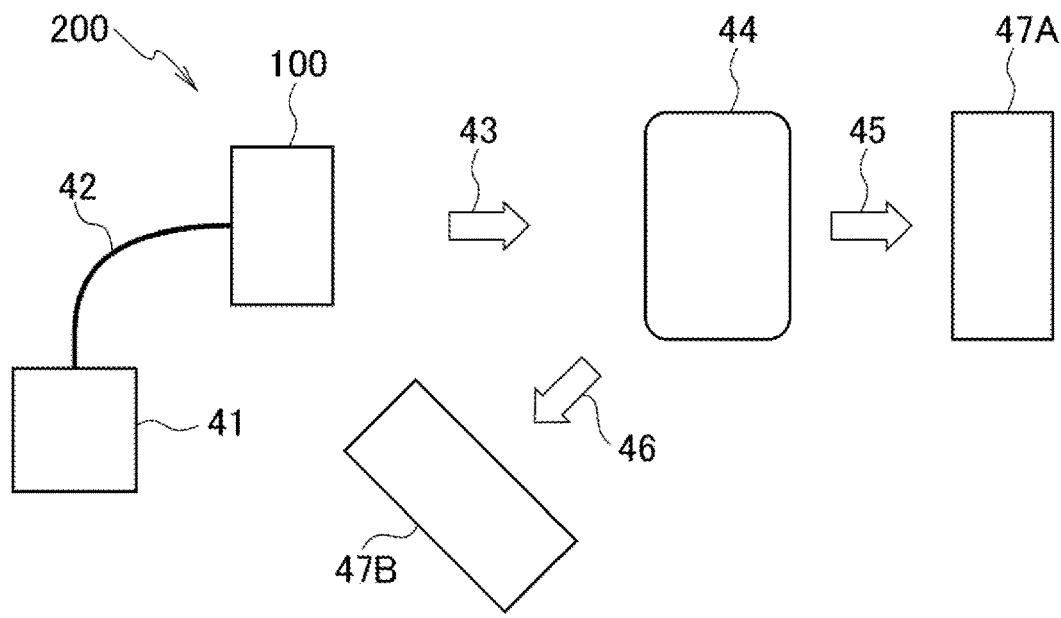
FIG. 12 is a schematic diagram illustrating an example of an electronic instrument according to this embodiment.

Next, an electronic instrument according to this embodiment will be described. An electronic instrument according to this embodiment is provided with the light emitting device described above. FIG. 12 schematically illustrates an example of an electronic instrument according to this embodiment. An electronic instrument 200 is provided with at least a power source circuit 41, a conductor 42, and the light emitting device 100 provided with the wavelength converting composite member, rotation drive device, and solid-state light emitting element.

The power source circuit 41 supplies power to the rotation drive device and solid-state light emitting element in the light emitting device. Furthermore, the power source circuit 41 supplies electrical energy to the rotation drive device and solid-state light emitting element via the conductor 42.

The light emitting device 100 converts electrical energy into light energy, as mentioned above. The light emitting device 100 converts at least part of the electrical energy supplied from the power source circuit 41 into light energy and outputs the light energy as output light 43. Note that the light emitting device 100 in FIG. 12 is configured to emit output light 43 that includes near-infrared light.

The electronic instrument 200 in FIG. 12 is further provided with a first detector 47A and a second detector 47B. The first detector 47A detects a transmitted light component 45 of the output light 43 radiated from the light emitting device 100 onto an irradiated object 44. Specifically, the first detector 47A detects near-infrared light in the transmitted light component 45 that has passed through the irradiated object 44. The second detector 47B detects a reflected light component 46 of the output light 43 radiated from the light emitting device 100 onto the irradiated object 44. Specifically, the second detector 47B detects near-infrared light in the reflected light component 46 that has been reflected by the irradiated object 44.

In the electronic instrument 200 having this kind of configuration, the output light 43 including a near-infrared light component is radiated on the irradiated object 44, and the transmitted light component 45 that has passed through the irradiated object 44 and the reflected light component 46 reflected by the irradiated object 44 are detected by the first detector 47A and the second detector 47B, respectively. Therefore, by means of the electronic instrument 200, it becomes possible to detect information regarding characteristics of the irradiated object 44 involving the near-infrared light component.

Here, the light emitting device of this embodiment can emit the output light 43, which includes visible light and near-infrared light and is convenient for both the human eye and a detector. Therefore, combining the light emitting device and a near-infrared ray detector results in an electronic instrument that is suitable for industrial uses.

Furthermore, the light emitting device of this embodiment can be configured such that the energy of the output light 43 is high and a wide range is illuminated. Therefore, even if the output light 43 is radiated on the irradiated object 44 from a distance away, a signal having a good S/N ratio (signal/noise ratio) can be detected. Thus, the electronic instrument is suitable for the inspection of a large irradiated object 44, the batch inspection of objects distributed over a wide area, the detection of objects present in part of an inspection area covering a wide area, the detection of people and objects from a distance, and so forth.

For reference, when describing the size of the light emitting device of this embodiment, for example, the area of a main light extraction surface of the light emitting device 100 can be 1 cm$^2$ or more and less than 1 m$^2$, preferably 10 cm$^2$ or more and less than 1000 cm$^2$. Furthermore, the minimum distance from the light emitting device 100 to the irradiated object 44 is 1 mm or more and less than 10 m, for example. In the case where it is necessary for the irradiated object 44 to be irradiated with an intense near-infrared ray, for example, in cases of medical, cosmetic, and delicate foreign substance inspections, the minimum distance from the light emitting device 100 to the irradiated object 44 can be 1 mm or more and less than 30 cm, preferably 3 mm or more and less than 10 cm, for example. In addition, in the case where it is necessary to inspect an irradiated object 44 of a wide range, the minimum distance from the light emitting device 100 to the irradiated object 44 can be 30 cm or more and less than 10 m, preferably 1 m or more and less than 5 m.

Note that in the case where it is necessary to radiate an intense near-infrared ray over a wide range, it is preferable that the light emitting device 100 be configured to be movable, and it is even more preferable that it be configured to be able to move freely according to the form of the object to be illuminated. For example, the light emitting device 100 can have a structure that enables coming and going on a straight or curved line, a structure that enables scanning in the XY axial directions or the XYZ directions, or a structure attached to a mobile body (automobile, bicycle, or flying body such as a drone).

Various types of photodetectors can be used for the first detector 47A and the second detector 47B. Specifically, depending on the form of use of the electronic instrument, it is possible to use a quantum-type photodetector (photodiode, phototransistor, photo IC, CCD image sensor, CMOS image sensor, or the like) that detects the charge generated when light is input to a PN junction of a semiconductor. Furthermore, as a photodetector, it is also possible to use a thermal-type photodetector (thermopile using the thermoelectric effect, pyroelectric element using the pyroelectric effect, or the like) that detects change in an electrical property caused by a temperature increase due to heat generated when light is received, an infrared film that is sensitive to light, or the like.

As the first detector 47A and the second detector 47B, a single element using a single photoelectric conversion element may be used, or an imaging element having an integrated photoelectric conversion element may be used. The imaging element may have a linear form disposed in one dimension, or may have a planar form disposed in two dimensions. An imaging camera can also be used as the first detector 47A and the second detector 47B.

Note that although the electronic instrument 200 of FIG. 12 is provided with both the first detector 47A and the second detector 47B, it is sufficient for the electronic instrument to be provided with at least one of the first detector 47A or the second detector 47B.

Furthermore, the electronic instrument of this embodiment can be used as an inspection device, detection device, monitoring device, or a sorting device for irradiated objects using the output light. The near-infrared light component of the output light has the property of passing through most substances. Therefore, by adopting a configuration in which near-infrared light is radiated from outside of a substance and the transmitted light or reflected light is detected, the internal state, the presence or absence of foreign substances, and so forth can be inspected without destroying the substance.

Furthermore, a near-infrared light component is invisible to the human eye, and its reflection characteristics are dependent on the substance. Therefore, by adopting a configuration in which an object is irradiated with near-infrared light and the reflected light is detected, it is possible to detect people, flora and fauna, objects, and the like even in the dark and so forth without being perceived by humans.

In addition, the electronic instrument of this embodiment can inspect the internal state of substances, the presence or absence of foreign substances, and so forth, determine the quality of substances, and select good-quality products and defective products, without destroying substances. It is therefore possible for the electronic instrument to sort objects by further providing a mechanism to sort irradiated objects of a normal state and irradiated objects of an abnormal state.

In the electronic instrument of this embodiment, it is also possible for the light emitting device 100 to be fixed without being made movable. In this way, it is not necessary for the light emitting device to be provided with a complicated mechanism for mechanically moving the light emitting device, therefore resulting in an electronic instrument that is unlikely to malfunction. Furthermore, by fixing the light emitting device indoors or outdoors, it is possible to observe the state of people and objects in a predetermined location from a fixed point, and to count the number of people and objects. Therefore, the electronic instrument is advantageous for collecting big data that is useful for discovering problems, for business applications, and so forth.

The electronic instrument of this embodiment can also be used to make the light emitting device 100 movable and change the location of irradiation. For example, the light emitting device 100 can be made movable by attachment to a mobile stage or a mobile body (vehicle, flying body, or the like). In this way, the light emitting device 100 can illuminate a desired location or a wide range, therefore resulting in an electronic instrument that is advantageous for inspecting large objects and inspecting the state of objects outdoors.

The electronic instrument of this embodiment can have a configuration further provided with a hyperspectral camera as an imaging camera, in addition to the light emitting device. The electronic instrument is thereby able to perform hyperspectral imaging. An electronic instrument provided with a hyperspectral camera can distinguish, as images, differences that cannot be determined by the naked eye or an ordinary camera, therefore resulting in an inspection device that is useful in a wide range of fields related to the inspection, selection, and so forth of products.

Figure 13:
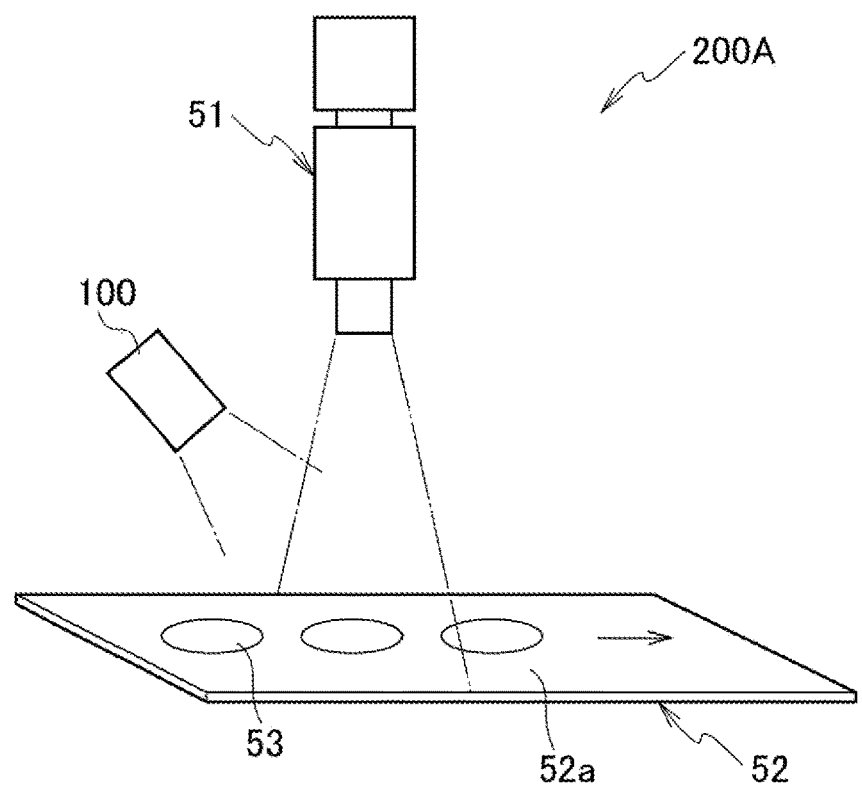
FIG. 13 is a perspective view schematically illustrating another example of an electronic instrument according to this embodiment.

Specifically, as illustrated in FIG. 13, an electronic instrument 200A is provided with the light emitting device 100 and a hyperspectral camera 51. Irradiated objects 53 that are placed on a surface 52a of a conveyor 52 are then captured by the hyperspectral camera 51 while output light is radiated from the light emitting device 100 to the irradiated objects 53. By analyzing obtained images of the irradiated objects 53, the irradiated objects 53 can be inspected and selected.

It is also preferable that the electronic instrument of this embodiment be further provided with a data processing system that performs machine learning, in addition to the light emitting device. It thereby becomes possible to iteratively learn data imported into a computer and to discover patterns hidden therein. Furthermore, it also becomes possible to adapt newly captured data to those patterns. Therefore, the electronic instrument is advantageous for implementing automation and achieving higher accuracy in inspection, detection, monitoring, and the like, and also for future prediction using big data.

The electronic instrument of this embodiment can be used for medical uses, veterinary uses, biotechnology uses, agriculture, forestry, and fishery industry uses, livestock industry uses (meat, meat products, dairy products, and the like), and manufacturing industry uses (foreign substance inspection, content quantity inspection, shape inspection, packaging state inspection, and the like). Furthermore, the electronic instrument can also be used for inspection of pharmaceutical products, animal testing, food products, beverages, agriculture, forestry, and fishery products, livestock products, and industrial products. In other words, the electronic instrument of this embodiment can also be used on any of the human body, flora and fauna, and objects, and in addition can also be used on any of gases, liquids, and solids.

The electronic instrument of this embodiment is preferably used as a medical device, a treatment device, a beauty device, a health device, a care-related device, an assay device, a measurement device, or an evaluation device.

For example, for medical and biotechnology development purposes, the electronic instrument of this embodiment can be used for inspection, detection, measurement, evaluation, assay, analysis, observation, monitoring, separation, diagnosis, treatment, purification, and so forth for the following: 1) blood, body fluids, and their components; 2) excretions (urine and feces); 3) proteins and amino acids; 4) cells (including cancer cells); 5) genes, chromosomes, and nucleic acids; 6) biological samples, bacteria, specimens, and antibodies; 7) biological tissue, organs, and blood vessels; and 8) skin diseases and alopecia.

Furthermore, for example, for beauty and health care purposes, the electronic instrument of this embodiment can be used for inspection, detection, measurement, evaluation, assay, analysis, observation, monitoring, beautification, sanitation, growth promotion, health promotion, diagnosis, and so forth for the following: 1) skin; 2) hair and body hair; 3) oral, endodontic, and periodontal conditions; 4) ears and nose; and 5) vital signs.

For example, for purposes of the agriculture, forestry, and fishery industry, the livestock industry, and the manufacturing industry, the electronic instrument of this embodiment can be used for inspection, detection, measurement, quantification, evaluation, assay, analysis, observation, monitoring, recognition, selection, sorting, and so forth for the following: 1) industrial products (including electronic members and electronic devices); 2) agricultural products (such as fruits and vegetables); 3) enzymes and bacteria; 4) marine products (fish, shellfish, crustaceans, and mollusks); 5) pharmaceutical products and biological samples; 6) food products and beverages; 7) the presence and state of people, animals, and objects; 8) the state of gases (including water vapor); 9) liquids, fluids, water, moisture, and humidity; 10) the shape, color, internal structure, and physical state of objects; 11) space, position, and distance; 12) the contamination state of objects; 13) the state of molecules and particles; and 14) 13) industrial waste.

For example, for caregiving purposes, the electronic instrument of this embodiment can be used to confirm excretion and for the identification, management, monitoring, and so forth of health conditions.

In this way, the electronic instrument of this embodiment can be used for all kinds of uses such as inspection, detection, measurement, quantification, evaluation, assay, analysis, observation, monitoring, recognition, selection, and sorting.

The present embodiment has been described above, but the present embodiment is not limited to the above description, and various variations are possible within the scope of the gist of the present embodiment.

The entire contents of Japanese Patent Application No. 2020-076772 (filed on: Apr. 23, 2020) are incorporated herein by reference.

INDUSTRIAL APPLICABILITY

According to the present disclosure, it is possible to provide a wavelength converting composite member with which a substrate provided with a wavelength converting member can be rotated smoothly to improve reliability, and to provide a light emitting device and an electronic instrument using the wavelength converting composite member.

REFERENCE SIGNS LIST 10, 10A, 10B, 10C, 10D, 10E, 10F. Wavelength converting composite member
11 First wavelength converting member
12 Second wavelength converting member
13 Substrate
13a Main surface
14 Weight member
20 Solid-state light emitting element
100 Light emitting device
200, 200A Electronic instrument

The invention claimed is:

1. A wavelength converting composite member, comprising:
a disk-shaped substrate;
a first wavelength converting member provided on the substrate and containing a first phosphor that radiates fluorescence due to a parity-forbidden transition; and
a second wavelength converting member provided on the substrate and containing a second phosphor that radiates fluorescence due to a parity-allowed transition,
wherein the first wavelength converting member and the second wavelength converting member are disposed adjacent to each other along a circumferential direction of the substrate, and
wherein the first wavelength converting member and the second wavelength converting member are provided on the substrate in such a way that a position of a center of gravity of an entirety of the first wavelength converting member and the second wavelength converting member is located on a rotation axis of the substrate.

2. The wavelength converting composite member according to claim 1, wherein the first wavelength converting member has a greater thickness than the second wavelength converting member in a direction perpendicular to a main surface of the substrate.

3. The wavelength converting composite member according to claim 1, wherein an area occupied by the second wavelength converting member is larger than an area occupied by the first wavelength converting member when viewed along the rotation axis of the substrate.

4. The wavelength converting composite member according to claim 1, wherein, by providing a weight member that does not include the first phosphor and the second phosphor, near the second wavelength converting member, a position of a center of gravity of an entirety of the first wavelength converting member, the second wavelength converting member, and the weight member is located on the rotation axis of the substrate.

5. The wavelength converting composite member according to claim 1,
wherein the first wavelength converting member and the second wavelength converting member are each divided into a plurality of parts, and
wherein the first wavelength converting member and the second wavelength converting member are disposed in an alternating manner along the circumferential direction of the substrate.

6. The wavelength converting composite member according to claim 1, wherein, in a direction perpendicular to a main surface of the substrate, a height from a main light output surface of the first wavelength converting member to the main surface of the substrate is the same as a height from a main light output surface of the second wavelength converting member to the main surface of the substrate.

7. The wavelength converting composite member according to claim 1, wherein the substrate is light-reflective.

8. The wavelength converting composite member according to claim 1, wherein the substrate is translucent.

9. A light emitting device, comprising the wavelength converting composite member according to claim 1.

10. The light emitting device according to claim 9, further comprising a solid-state light emitting element that radiates light with which the first wavelength converting member and the second wavelength converting member are irradiated.

11. The light emitting device according to claim 9, wherein the light emitting device is a medical light emitting device.

12. An electronic instrument, comprising the light emitting device according to claim 9.

* * * * *